United States Patent [19]
Schirmer

[11] Patent Number: 5,769,840
[45] Date of Patent: Jun. 23, 1998

[54] MICROSURGERY USING ALTERNATING DISRUPTIVE AND THERMAL LASER BEAM PULSES

[76] Inventor: Kurt E. Schirmer, 56 Granville Road, Hampstead, Quebec, Canada, H3X 3B6

[21] Appl. No.: 446,150

[22] Filed: May 22, 1995

Related U.S. Application Data

[63] Continuation of Ser. No. 281,510, Jul. 28, 1994, abandoned, which is a continuation of Ser. No. 929,440, Aug. 14, 1992, abandoned, which is a continuation-in-part of Ser. No. 183,049, Apr. 19, 1988, abandoned.

[51] Int. Cl.$^6$ .................................................. A61N 5/06
[52] U.S. Cl. .................................. 606/3; 606/2; 606/10; 606/13
[58] Field of Search ....................................... 606/2, 3–18

[56] References Cited

U.S. PATENT DOCUMENTS

| | | |
|---|---|---|
| 3,693,623 | 9/1972 | Harte et al. . |
| 3,982,541 | 9/1976 | L'Esperance ............................... 606/4 |
| 4,672,969 | 6/1987 | Dew ........................................... 606/3 |
| 5,122,135 | 6/1992 | Dürr et al. . |
| 5,125,922 | 6/1992 | Dwyer et al. ............................. 606/3 |
| 5,312,396 | 5/1994 | Feld et al. ................................. 606/3 |

FOREIGN PATENT DOCUMENTS

| | | |
|---|---|---|
| 2043072 | 5/1991 | Canada . |
| 3904287 | 9/1989 | Germany . |
| WO 92/20288 | 11/1992 | WIPO . |

OTHER PUBLICATIONS

"Laser Photodisruptors Damage Mechanisms, Instrument Design and Safety" Martin A. Mainster, MD,Ph.D., Reprinted from: Ophthalmology, vol. 90, No. 8, Aug. 1983.

Ophthalmologica 1990;200:57–62 "Scleral Incision by Alternating Argon and Nd:YAG Laser", by K.E. Schirmer.

Ophthalmologica 1992;205:169–177 "Stimultaneous Thermal and Optical Breakdown Mode Dual Laser Action" by K.E. Schirmer.

SPIE vol. 712 Lasers in Medicine (1986) pp. 200–205, "Pulse Width Dependence of Pigment Cell Damage at 694 nm in Guinea Pig Skin" by Jeffrey S. Dover et al.

*Primary Examiner*—David M. Shay
*Attorney, Agent, or Firm*—Michael D. Bednarek; Kilpatrick Stockton LLP

[57] ABSTRACT

A method and an apparatus for conducting microsurgery on human or animal tissue which includes alternately providing an Argon laser beam pulse and a YAG laser beam pulse in a cycle which is equal to or less than one second. A robotic device including piston and cylinder arrangements is provided for activating the control keys on a control panel associated with the Argon and YAG lasers.

10 Claims, 1 Drawing Sheet

MICROSURGERY USING ALTERNATING DISRUPTIVE AND THERMAL LASER BEAM PULSES

CROSS-REFERENCE TO RELATED APPLICATION

This is a continuation application of application Ser. No. 08/281,510 filed Jul. 28, 1994, now abandoned which is a continuation of application Ser. No. 07/829,440 filed Aug. 14, 1992, now abandoned which is a continuation in part of application Ser. No. 07/183,049 filed Apr. 19, 1988, now abandoned.

BACKGROUND OF THE INVENTION

1. Field of the Invention

The present invention relates to a method and apparatus for conducting microsurgery, and in particular, for incising human and animal tissue with a focused light beam.

2. Description of the Prior Art

In particular, because of sharp focusing and high power, laser beams are at present used to incise material. Thus, on the one hand, laser beams are used in the manufacture of components for electronics, and in particular, in the manufacture of integrated circuits. In medicine, and particularly in ophthalmology, they are used for heat coagulating the retina and disrupting a membrane of a cataract.

If lasers, with laser beams of long pulse duration, are used (e.g., thermal lasers), the energy converted at the target point as heat also has an effect in the adjacent areas whereby a desirable heat coagulation of the incision walls is achieved, but undesirable material changes can occur outside the incision.

If lasers with very high power laser beams are used (e.g., solid state lasers), rapid incisions can be made. However, the incision walls can be very unstable, particularly in soft materials, since the incision walls have not undergone any stabilization by heat.

In the case of materials containing much fluid, such as plant substances, human or animal tissue, fluid, such as blood, etc., penetration into the incision is effected when incising by means of a high power laser beam which is not coagulated, thus leading to problems, in particular, hindrances in the application of a laser.

When the tissues of the human eye or of the human or animal body are subjected to repeated applications of a thermal (long pulse duration) or a photodisruptive type of laser, it becomes obvious that the same laser discharge on the same tissue achieves progressively diminished results. In the case of the thermal (Ar) laser, it is due to an increased blanching of the tissue that the beam is reflected. In the case of the photodisruptive laser (YAG), it is the debris within the cut created by the laser and pressure from the adjacent tissue that prevents efficient tissue tunneling. Neither type of laser is able to achieve by itself efficient tunneling through solid tissue from a distance without direct contact.

Surgical treatment requires the ability to create channels through solid tissue to form shunts and bypasses for the passage of body fluids or to penetrate through tissue to reach the object of surgery.

SUMMARY OF THE INVENTION

It is an object of the present invention to provide an apparatus for incising with a sharply focused laser beam, with which in particular blood fluid containing high tissue can be cut with high efficiency.

A method in accordance with the present invention includes the steps of causing an incision in animal or human tissue comprising the steps of producing a first laser beam from a laser source consisting of one of a photodisruptive laser and a thermal laser directing the first laser beam to the target area for a predetermined pulse duration and immediately successively producing a second laser beam from a second source consisting of the other photodisruptive laser and the thermal laser for a pulse of a predetermined duration to complete a cycle for a complete duration of one second or less, and repeating the cycle.

In a more specific embodiment of the present method, the first and second laser beams are directed confocally onto the target area in alternating pulses.

An apparatus in accordance with the present invention comprises a housing, a first laser means producing a photodisruptive laser beam, a second laser means producing a thermal laser beam, means for directing the laser beams from the first and second laser means along a confocal path from the housing to a target, switching means for alternately directing the photodisruptive beam and the thermal beam in successive pulse durations for a complete cycle of a duration of one second or less.

In a more specific embodiment of the present invention, the thermal laser is an Argon laser while the photodisruptive laser is an Nd:YAG laser.

The alternative application of different types of lasers is of advantage. The energy of the laser beam of the thermal laser is converted in the tissue to heat.

It has been found that the alternating treatment of successive Argon laser beams and YAG laser beams allows a deeper incision in the tissue. If a YAG laser discharge precedes an Argon laser application, the YAG laser cuts the tissue while the Argon laser coagulates the tissue. The cut of the YAG laser then penetrates the photocoagulated tissue at the target and reaches a deeper stratum which is not affected by the previous coagulation. The Argon laser beam passes through the incision and is efficiently absorbed, and the repeated alternating effect of the Argon-YAG laser discharges creates a cavity in the tissue with coagulated tissue walls.

The subsequent discharge of photodisruptive energy by the YAG laser of a second alternating cycle provides an implosive force within the same space. It disrupts the coagulated walls and expands the tunneling further. This action creates favourable conditions for another alternating laser cycle for further penetration.

The combined forces of the alternating beams is greater than each separate laser can provide alone. The explosive force of the Argon laser discharge is followed by the YAG laser's implosive force. The efficient transformation of these forces into mechanical energy prevents laser radiation overdosage.

It has been found that the alternating cycle of the laser beams must be accomplished within a time span of less than one second.

BRIEF DESCRIPTION OF THE DRAWINGS

Having thus generally described the nature of the invention, reference will now be made to the accompanying drawings, showing by way of illustration, a preferred embodiment thereof, and in which.

DESCRIPTION OF THE PREFERRED EMBODIMENTS

Figure 1:
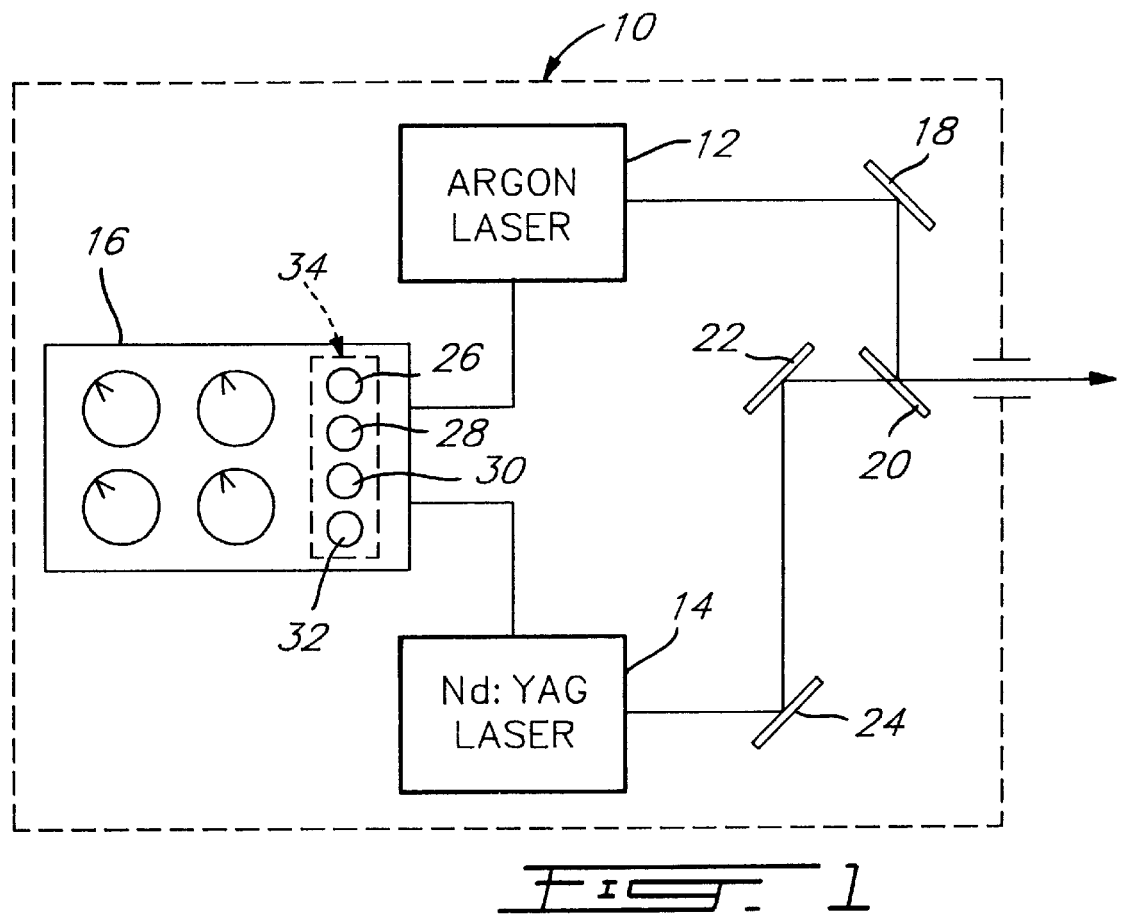
FIG. 1 schematic diagram of a typical arrangement for producing two alternating laser beams of different wave lengths.
Figure 2:
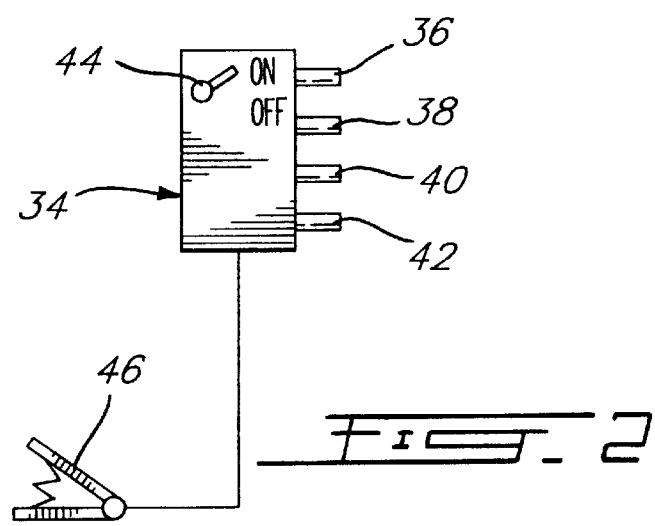
FIG. 2 a schematic diagram of a typical robotic switching device which could be used with the apparatus illustrated schematically in FIG. 1.

Referring now to the drawings, there is shown a housing 10 within which is provided a typical Argon laser 12 and an Nd:YAG laser 14. A control panel 16 is arranged in the housing. The control panel includes manual command keys for the YAG laser (COHERENT System 9900). These command keys may include a STANDBY key 26 and a DISCHARGE key 28. A READY key 30 and an ARGON key 32 are also provided in line on the control panel. A robotic switching device 34, as shown in FIG. 2, would be located over the manual keys as shown in dotted lines in FIG. 1. The robotic device 34 would include piston and cylinder arrangements 36, 38, 40, and 42, which correspond to manual keys 26, 28, 30, and 32. The piston and cylinder arrangements, as is well known, may be pneumatic and may be electronically or electrically activated and may be controlled by a computer (not shown).

In order that the beams produced respectively from the Argon laser 12 and the YAG laser 14 be confocal, a series of mirrors 18, 20, 22, and 24, which are well known from the prior art, are located in order to direct the laser beams as required. An on-off trigger 44 activates the sequence, but a controlling foot switch 46 may be provided in order to include a double safety control.

The robotic device 34 is included in order to provide a cycle within one second which includes in one typical sequence the activation of the STANDBY key 26 by means of the corresponding piston 36 in the robot device 34 followed by the activation of the ARGON key 32 by the respective piston 42. This activation will provide the first laser discharge, and then the READY key 28 must be activated by the respective piston 38 in order to discharge the YAG laser beam by means of the YAG key 30. The cycle is repeated by starting over again with the STANDBY key 26.

I claim:

1. An apparatus for causing an incision on human or animal tissue, comprising:

first and second laser beam source means producing a first laser beam for photocoagulation and a second laser beam for photodisruption;

means for directing the laser beams from the first and second laser source means along a confocal path to a target on said tissue;

switching means for controlling said first and second laser beam source means for directing the first laser beam to said target for a predetermined photodisruptive pulse duration and for directing the second laser beam to said target for predetermined thermal pulse duration to repeatedly complete a controlled cycle having a period of one second or less, whereby the second laser beam pulse coagulates tissue and the first laser beam pulse penetrates further through the coagulated tissue and cuts deeper by disruption, thereby permitting the second laser beam pulse subsequently to be efficiently absorbed, whereby efficient tunneling through solid tissue with a predictable size is provided.

2. An apparatus as defined in claim 1, wherein the first and second laser beam source means comprise an Argon laser for the first laser beam.

3. An apparatus as defined in claim 1, wherein the first and second laser beam source means comprise a Nd:YAG laser for the second laser beam.

4. An apparatus as defined in claim 1, wherein the first and second laser beam source means comprise an Argon laser for the first laser beam and an Nd:YAG laser for the second laser beam.

5. An apparatus as defined in claim 4, wherein the switching means include a robotic device including a plurality of piston and cylinder arrangements for actuating manual keys on a control panel of said Argon and Nd:YAG lasers, and means for cyclically controlling said robotic device to produce said first and second laser beams for said photodisruptive and thermo pulse durations respectively.

6. A method of incising human and animal tissue comprising the steps of:

providing a source of a first laser beam for tissue photocoagulation and a second laser beam for tissue photodisruption;

producing and directing the first laser beam to a target area on said tissue for a predetermined photodisruptive pulse duration, producing and directing the second laser beam to the target area for a predetermined thermal pulse duration to complete a cycle having a period of one second or less; and repeating the cycle, wherein the second laser beam pulse coagulates tissue and the first laser beam pulse penetrates further through the coagulated tissue and cuts deeper by disruption, thereby permitting the second laser beam pulse subsequently to be efficiently absorbed, whereby efficient tunneling through solid tissue with a predictable size is provided.

7. A method as defined in claim 6, wherein the second laser beam source is an Argon laser.

8. A method as defined in claim 6, wherein the first and second laser beams are directed confocally onto the target area in alternating pulses.

9. A method as defined in claim 6, wherein the first laser beam source is an Nd:YAG laser.

10. A method as defined in claim 9, wherein the second laser beam source is an Argon laser.

* * * * *